US009448150B2

(12) United States Patent
Estrada et al.

(10) Patent No.: US 9,448,150 B2
(45) Date of Patent: Sep. 20, 2016

(54) METHOD AND APPARATUS FOR DETERMINING KINEMATIC VISCOSITY THROUGH THE TRANSMISSION AND RECEPTION OF ULTRASONIC ENERGY

(71) Applicants: Herbert A. Estrada, Annapolis, MD (US); Donald R. Augenstein, Pittsburgh, PA (US); Bobbie W. Griffith, Harrisville, PA (US); Calvin R. Hastings, Mt. Lebanon, PA (US)

(72) Inventors: Herbert A. Estrada, Annapolis, MD (US); Donald R. Augenstein, Pittsburgh, PA (US); Bobbie W. Griffith, Harrisville, PA (US); Calvin R. Hastings, Mt. Lebanon, PA (US)

(73) Assignee: Cameron International Corporation, Houston, TX (US)

( * ) Notice: Subject to any disclaimer, the term of this patent is extended or adjusted under 35 U.S.C. 154(b) by 276 days.

(21) Appl. No.: 14/171,394

(22) Filed: Feb. 3, 2014

(65) Prior Publication Data

US 2015/0219541 A1 Aug. 6, 2015

(51) Int. Cl.
*G01N 29/02* (2006.01)
*G01N 11/00* (2006.01)
*G01N 29/032* (2006.01)

(52) U.S. Cl.
CPC ............... *G01N 11/00* (2013.01); *G01N 29/02* (2013.01); *G01N 29/032* (2013.01); *G01N 2011/0073* (2013.01); *G01N 2291/011* (2013.01); *G01N 2291/014* (2013.01); *G01N 2291/02818* (2013.01)

(58) Field of Classification Search
CPC .... G01N 11/00; G01N 11/16; G01N 29/032; G01N 29/02; G01N 2291/02; G01N 2291/02836; G01N 2291/011; G01N 2291/014; G01N 2291/02818
USPC .............. 73/54.41, 64.42, 64.53, 61.79, 592
See application file for complete search history.

(56) References Cited

U.S. PATENT DOCUMENTS

| | | | | |
|---|---|---|---|---|
| 3,779,070 A * | 12/1973 | Cushman | ............. | G01N 29/032 73/628 |
| 4,320,659 A * | 3/1982 | Lynnworth | ............... | G01F 1/66 73/290 V |
| 4,331,025 A * | 5/1982 | Ord, Jr. | ...................... | G01F 1/66 73/54.01 |
| 4,559,810 A * | 12/1985 | Hinrichs | .................. | B01J 3/002 73/54.41 |
| 4,763,525 A * | 8/1988 | Cobb | ..................... | G01N 15/10 73/19.03 |
| 5,365,778 A * | 11/1994 | Sheen | .................... | G01N 11/16 73/32 A |
| 5,686,661 A * | 11/1997 | Singh | ..................... | G01N 11/00 73/54.02 |
| 6,227,040 B1 * | 5/2001 | Hastings | .............. | G01N 29/032 73/54.41 |
| 6,305,233 B1 * | 10/2001 | Braathen | ................. | G01F 1/667 73/861.27 |
| 2002/0088953 A1 * | 7/2002 | Kensey | .............. | A61B 5/02035 250/577 |
| 2008/0208483 A1 * | 8/2008 | Loose | ..................... | G01F 1/666 702/22 |
| 2011/0023625 A1 * | 2/2011 | Weinstein | ................. | G01F 1/74 73/861.357 |

* cited by examiner

Primary Examiner — Helen Kwok
(74) Attorney, Agent, or Firm — Ansel M. Schwartz (57) ABSTRACT

An apparatus for determining a fluid's kinematic viscosity from ultrasonic energy that has passed through the fluid of unknown viscosity along an acoustic path of known length. A computer of the apparatus determines a characteristic frequency of a received electrical signal associated with the ultrasonic energy and measures the fluid's velocity of sound. The kinematic viscosity of the fluid is determined by the computer on a continuous basis based on the characteristic frequency and the sound velocity. A method for determining a fluid's kinematic viscosity.

10 Claims, 7 Drawing Sheets

VISCOUS ATTENUATION AND UNFILTERED WAVEFORM SHOWN TOGETHER

FIG.3

NET WAVEFORM BANDWIDTH AFTER DIFFERENT AMOUNTS OF VISCOUS ATTENUATION

FLOW CHART OF THE CALCULATION OF REYNOLDS NUMBER AND
METER FACTOR CORRECTION FOR A CHORDAL ULTRASONIC METER

DURING FACTORY ACCEPTANCE AND CALIBRATION TESTS

- MEASURE RECEIVED SIGNAL TIME DEPENDENT PROPERTIES (FREQUENCY AND SOUND VELOCITY) AS NECESSARY TO CALCULATE THE FREQUENCY PARAMETER FOR AT LEAST TWO VISCOSITIES $FP = (1/v_0)(C_0/C)^3 (f/f_0)^2$
  HERE THE ZERO SUBSCRIPT INDICATES THE DATA TAKEN AT THE LOWEST VISCOSITY FLUID OF THE ACCEPTANCE TEST AND CALIBRATION PROCESS
- CONSTRUCT A LOG LINEAR CALIBRATION CURVE RELATING THE $LOG_{10}$(VISCOSITY-PATH LENGTH PRODUCT) TO THE FREQUENCY PARAMETER, FP
  $LOG(v\ L) = m \times FP + b$

---

IN THE FIELD

MEASURE RECEIVED SIGNAL TIME DEPENDENT PROPERTIES C AND f AS NECESSARY TO CALCULATE THE FREQUENCY PARAMETER.
C=PATH LENGTH/AVERAGE TRANSIT TIME IN THE FLUID
f=THE RECIPROCAL OF TWICE THE HALF PERIOD OF THE RECEIVED SIGNAL

CALCULATE THE FREQUENCY PARAMETERS $FP = (1/v_0)(C_0/C)^3 (f/f_0)^2$

DETERMINE:
- LOGARITHM TO THE BASE 10 OF VISCOSITY-PATH LENGTH PRODUCT, $LOG(v\ L)$
  $LOG(v\ L) = m \times FP + b$ COMPUTE
- THE LOGARITHM TO THE BASE 10 OF THE VISCOSITY OF THE FLOWING FLUID, $LOG(v)$
  $LOG(v) = LOG(v\ L) - LOG(L)$
COMPUTE LOG (v) AVERAGE:
- THE ARITHMETIC AVERAGE OF LOG (v).

MEASURE
- AVERAGE FLUID VELOCITY V USING BASE METER FACTOR MF
RETRIEVE
- INTERNAL DIAMETER ID FROM FLOW COMPUTATION
COMPUTE
- THE LOGARITHM OF THE REYNOLDS NUMBER LOG RN
  $LOG\ RN = LOG(V \times ID - LOG(v)$
  $\Delta LOG\ RN = LOG\ RN - LOG\ RN_0$
COMPUTE METER FACTOR MF LINEARIZED AS A FUNCTION OF LOG RD
- $MF = MF_0 + \Delta MF/\Delta LOG\ RN \times \Delta LOG\ RN$

*FIG.8*

METHOD AND APPARATUS FOR DETERMINING KINEMATIC VISCOSITY THROUGH THE TRANSMISSION AND RECEPTION OF ULTRASONIC ENERGY

FIELD OF THE INVENTION

The present invention is related to determining the kinematic viscosity of an unknown fluid using ultrasonic energy traveling along a known path length. (As used herein, references to the "present invention" or "invention" relate to exemplary embodiments and not necessarily to every embodiment encompassed by the appended claims.) More specifically, the present invention is related to determining the kinematic viscosity of an unknown fluid using ultrasonic energy traveling along a known path length, where from the ultrasonic energy, an associated characteristic frequency and sound velocity of the fluid is derived to determine the kinematic viscosity.

BACKGROUND OF THE INVENTION

This section is intended to introduce the reader to various aspects of the art that may be related to various aspects of the present invention. The following discussion is intended to provide information to facilitate a better understanding of the present invention. Accordingly, it should be understood that statements in the following discussion are to be read in this light, and not as admissions of prior art.

BRIEF SUMMARY OF THE INVENTION

The present invention uses the transmission and reception of acoustic signals that transit through an unknown fluid. The viscosity is computed with signal analysis in the frequency domain. The center frequency of the received signal is determined to be a function of the viscosity of the fluid medium and this frequency is compared with the received signal frequency measured in the laboratory for a product of a known viscosity.

BRIEF DESCRIPTION OF THE SEVERAL VIEWS OF THE DRAWING

In the accompanying drawings, the preferred embodiment of the invention and preferred methods of practicing the invention are illustrated in which:

FIG. 8 is a flow chart of the calculation of Reynolds Number and Meter Factor Correction for a chordal ultrasonic meter.

DETAILED DESCRIPTION OF THE INVENTION

Figure 7:
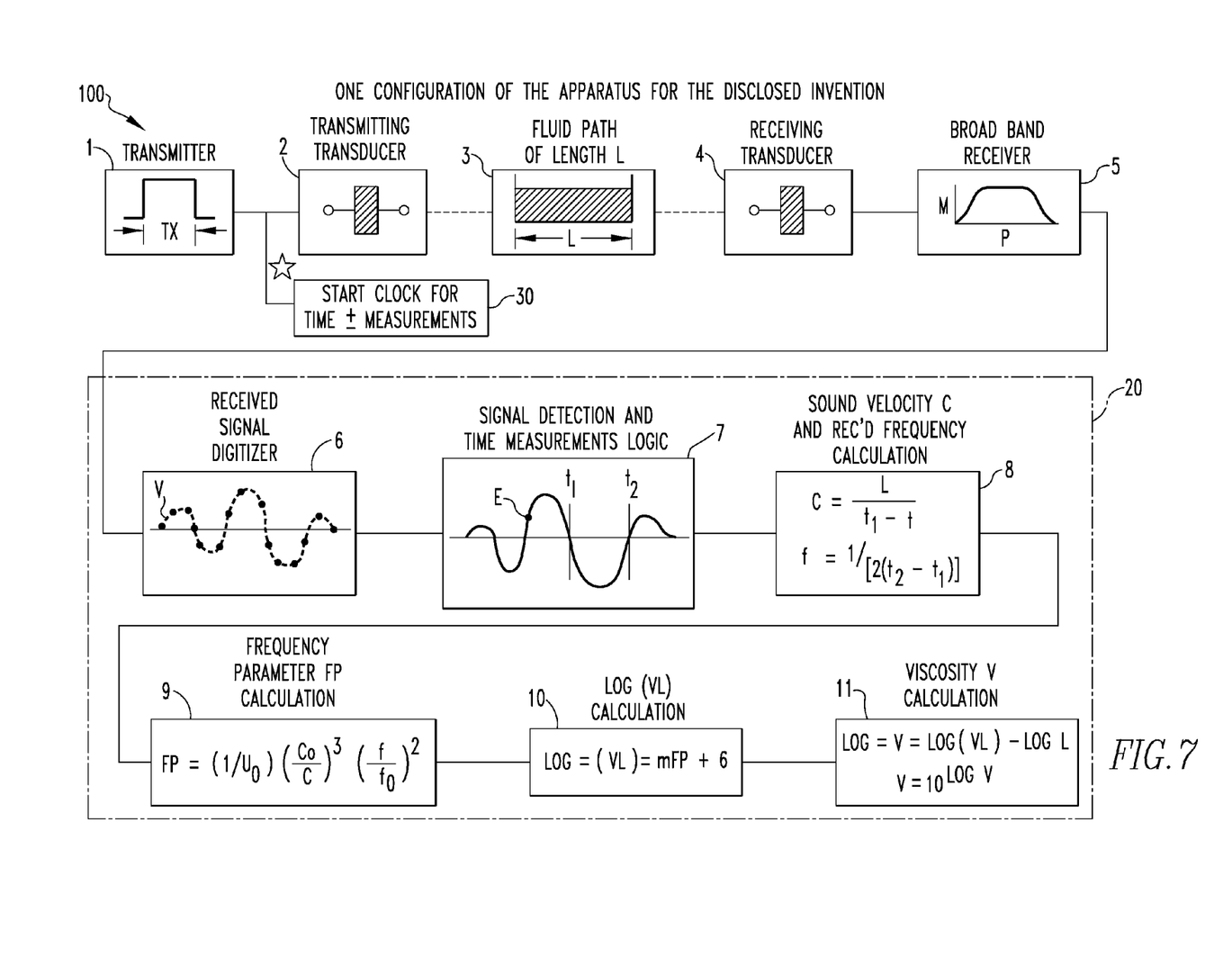
FIG. 7 is a block diagram of the apparatus of the present invention.

Referring now to the drawings wherein like reference numerals refer to similar or identical parts throughout the several views, and more specifically to FIG. 7 thereof, there is shown an apparatus 100 for determining a fluid's kinematic viscosity. The apparatus 100 comprises a transmitter 1 and transmitting transducer 2 capable of converting an input pulse from the transmitter 1 into ultrasonic energy. The apparatus 100 comprises a receiving transducer 4 and electronic amplifier 5 which convert some of the ultrasonic energy that has passed through the fluid of unknown viscosity into an electrical signal. The ultrasonic energy is created by the transducer follows an acoustic path 3 which is made to pass through the fluid of unknown viscosity along a path 3 of known length. The apparatus 100 comprises a computer 20 which determines a characteristic frequency of the received electronic electrical signal and measures the fluid's velocity of sound. The computer 20 determines kinematic viscosity of the fluid on a continuous basis based on the characteristic frequency and the sound velocity, where the kinematic viscosity is formed from the fluid's bulk viscosity and shear viscosity.

The bulk viscosity has a fixed relationship with the shear viscosity. The computer 20 may combine the characteristic frequency and sound velocity with similar data measured for a fluid of different viscosity and sound velocity to form a frequency parameter. The data may have been measured as part of a calibration process of the apparatus 100.

The computer 20 may determine a logarithm to an arbitrary base of a viscosity-path 3 length product for the fluid of unknown viscosity from the frequency parameter and from the data taken during calibration of the apparatus 100. The frequency parameter and the data may be used by the computer 20 to establish a slope and offset of the logarithm to the arbitrary base of a viscosity-path 3 length product versus frequency parameter relationship. The computer 20 may subtract a logarithm of the path 3 length from a logarithm of the viscosity path 3 length product to yield a result, and the computer 20 takes an antilog of the result, thereby determining the kinetic viscosity of the fluid. The computer 20 may include a received signal digitizer 6, signal detection and time measurement logic 7, sound velocity C and received frequency calculation module 8, frequency parameter (FP) calculation module 9, log (VL) calculation module 10, and viscosity calculation module 11.

The present invention pertains to a method for determining a fluid's kinematic viscosity. The method comprises the steps of triggering a transmitter 1 which generates an electrical transmit pulse. There is the step of commencing counting of timing pulses from a digital clock 30 simultaneous with the transmit pulse transmission. There is the step of applying the transmit signal via electrical cables to an ultrasonic transmitting transducer 2. There is the step of causing the transmitting transducer 2 with the transmit pulse to produce an ultrasonic pressure pulse having a limited number of sinusoidal cycles. The ultrasonic transmitting transducer 2 is mounted such that ultrasonic energy it produces travels through the fluid whose viscosity is to be measured along a path 3 of known length. There is the step of transferring at the end of the path 3 some of this energy to a receiving transducer 4. There is the step of converting with the receiving transducer 4 some of the ultrasonic energy into an electrical receive pulse. There is the step of amplifying by a receiver 5 the receive pulse whose frequency response is such that the energy content of all frequencies that are present in the receive pulse is preserved. There is the step of digitizing in a digitizer 6 the receive pulse. There is the step of reconstructing the receive pulse in digital format 7. There is the step of detecting a time of the receive pulse's arrival by signal detection logic. There is the step of measuring with a computer 20 transit time through the viscous fluid of the pressure pulse and transit time through non fluid media of the energy transmission path 3, including electrical delay of the cable between the transmitter 1 and the transmitting transducer 2, mechanical delay associated with an interface between the transmitting transducer 2 and the fluid, mechanical and cable delays associated with the receiving transducer 4 and electronic delays of the receiver 5. There is the step of calculating the fluid's sound velocity as a quotient of the path 3 length L through which the ultrasonic energy has traveled and the transit time of the ultrasonic energy in the fluid. There is the step of calculating a frequency parameter (FP) from the sound velocity and frequency measurements of the received ultrasonic energy pulse. There is the step of determining a Logarithm of a viscosity path 3 length product Log (vL) with the computer 20 from the Frequency Parameter with a log linear characteristic. There is the step of calculating with the computer 20 a kinematic viscosity v by subtracting the logarithm of the path 3 length from the Log (vL) to obtain a reminder, then taking an antilog of the reminder.

In the operation of the invention, kinematic viscosity of a flowing or stationary fluid is measured, a property not readily and reliably measured on a continuous basis.

Examples of the use of such a measurement may be for any or all of the following purposes:

Linearization of flow meters

Flowmeters such as turbine meters, helical turbine meters and ultrasonic meters may have Reynolds number dependent calibration curves. Knowledge of fluid viscosity allows the linearization of such meters, effectively widening their range and improving their accuracy.

Detection of feedstock properties for purposes of blending

In oil processing and other industries, real time control of additive injection to achieve a desired viscosity requires knowledge of the viscosity of the incoming feedstock as well as knowledge of the viscosity of the blend after injection of the additive.

Detection of viscosity of products entering a pipeline to establish pumping power surcharges The frictional losses in a pipeline are a direct function of the product viscosity. Pumping power is a major pipeline operating expense (the pumping power for a 30 inch diameter 1500 mile pipeline can approach 1100 MWe) and a batch surcharge based on product viscosity would be an equitable means for allocating energy costs.

Measurement of product viscosity for purposes of pipeline leak detection modeling Calculation of compressibility effects and determination of leak location require an accurate characterization of the pressure drop-flow characteristics of the pipeline and its products. The viscosity is a key variable in this characterization.

Unique requirements and properties of the present invention may include:

Excitation with a pulse signal to provide ultrasonic energy. Ultrasonic energy has a broad and defined frequency spectrum.

A receiver 5 having a broad and defined pass band.

A detection of received ultrasonic signals and measurement of center frequencies, for purposes of determining the characteristic frequency of the received signal. This measurement of frequency could be done either in the frequency domain, e.g., Fourier transform or in the time domain, e.g., signal period.

Measurement of the sound velocity of the medium having unknown viscosity.

Calibration by measuring the received frequencies in at least two different media of known or independently measured viscosities, one medium typically having low viscosity and the other having high viscosity.

Measurement of the sound velocities of the media used for calibration.

The principle of the present invention uses the transmission and reception of acoustic signals that transit through an unknown fluid. The viscosity is computed by signal analysis in the frequency domain. The center frequency of the received signal is determined to be a function of the viscosity of the fluid medium and this frequency may be compared with the received signal frequency measured in the laboratory for a product of a known viscosity.

The physical principles of the system will be described first. The system consists of:

(1) A transmitter 1 which supplies excitation to a transmitting transducer 2, (2) A transmitting transducer 2

(3) A fluid medium (When calibrating the device, two reference fluids are used, one typically has low kinematic viscosity (~1 cSt) and the other has a higher kinematic viscosity (2.5 to over 3000 cSt).

(4) A receiving transducer 4

(5) A receiver which amplifies and digitizes the received ultrasound. The receiver 5 may be equipped with (a) a low frequency stop filter, to eliminate noise at frequencies below the frequency range of interest for the measurement and (b) a high frequency stop filter.

(6) A computer 20

Sound Attenuation in a Viscous Medium

The intensity of an acoustic beam is attenuated in a viscous medium according to the following (Kinsler and Frey, "Fundamentals of Acoustics", Chapter 9, incorporated by reference herein):

$$Av = \exp(-2\alpha X) \quad \text{Equation (1)}$$

Where:

Av=Viscous attenuation factor

α=Attenuation coefficient

X=Acoustic path length in the medium

The number 2 appears in the expression because it describes the loss of acoustic energy (as opposed to pressure).

From the analysis of the cited reference, the following expression for the attenuation coefficient, α can be derived:

$$\alpha = \tfrac{2}{3}\omega^2 v/C^3 \quad \text{Equation (2)}$$

Where:

ω=Angular frequency of the ultrasound

ω=2πf, where f is the ultrasound frequency v=Kinematic viscosity

C=Sound velocity in the medium.

According to the cited reference, the kinematic viscosity of Equation (2) attenuates the ultrasound because of the combined effects of:

(a) The shear viscosity. At the pipe wall the axial velocity of the flowing fluid is diminished to zero from a representative free stream velocity by the friction between adjacent layers of the flowing fluid traveling at different axial velocities. The shear viscosity characterizes the frictional losses of flowing fluid in smooth pipe and determines the shape of the velocity profile, particularly near the pipe wall.

(b) The bulk kinematic viscosity. The previously cited reference also describes a second component of viscosity, which engenders losses in ultrasound transmitted through a viscous medium. This component has to do with the ultrasonic compression and expansion of the fluid at the molecular level.

The technique described herein finds the total kinematic viscosity—the combination of shear and bulk effects. As long as the bulk viscosity bears a fixed relationship to the shear viscosity (as it does in many families of fluids), the viscosity determined by the technique will be a valid index for the shear viscosity.

Rewriting Equation (1) below and substituting Equation (2) into it, the attenuation term becomes a function of frequency (where: $\omega=2\pi f$):

$$Av(\omega) = \exp\left(-\frac{4\omega^2 \nu X}{3C^3}\right) \quad \text{Equation (3)}$$

Figure 1:
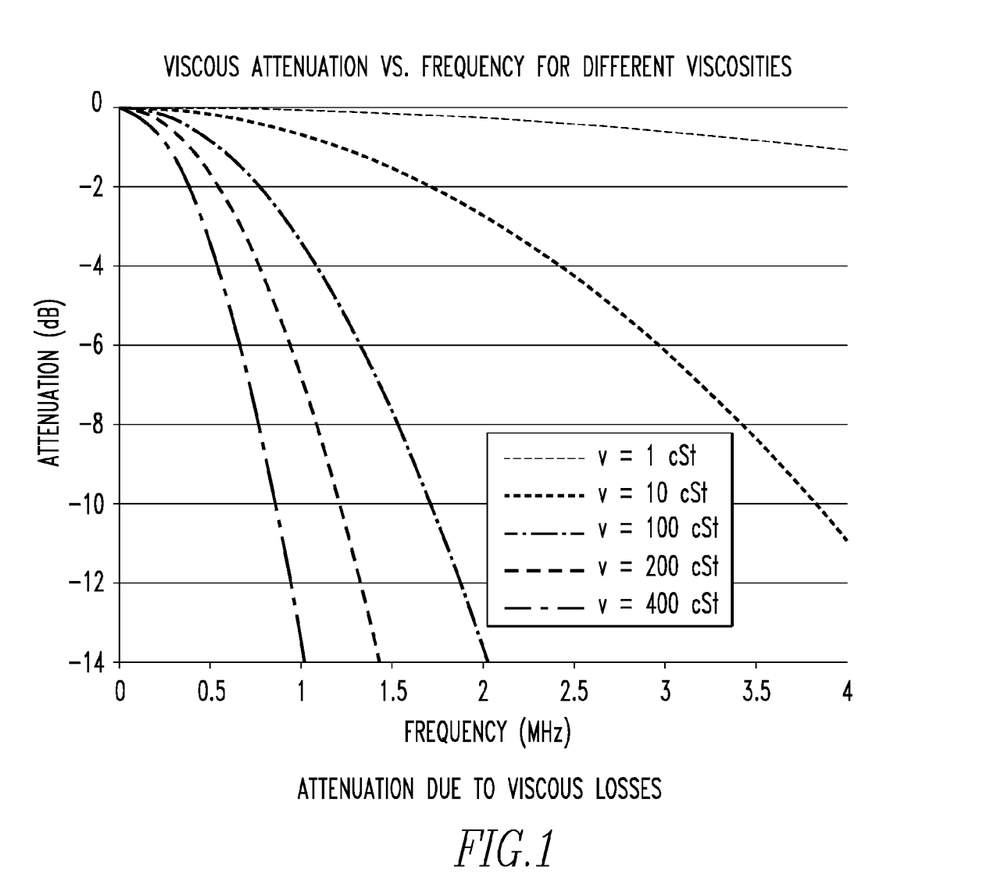
FIG. 1 is a graph showing attenuation due to viscous losses.
Figure 2:
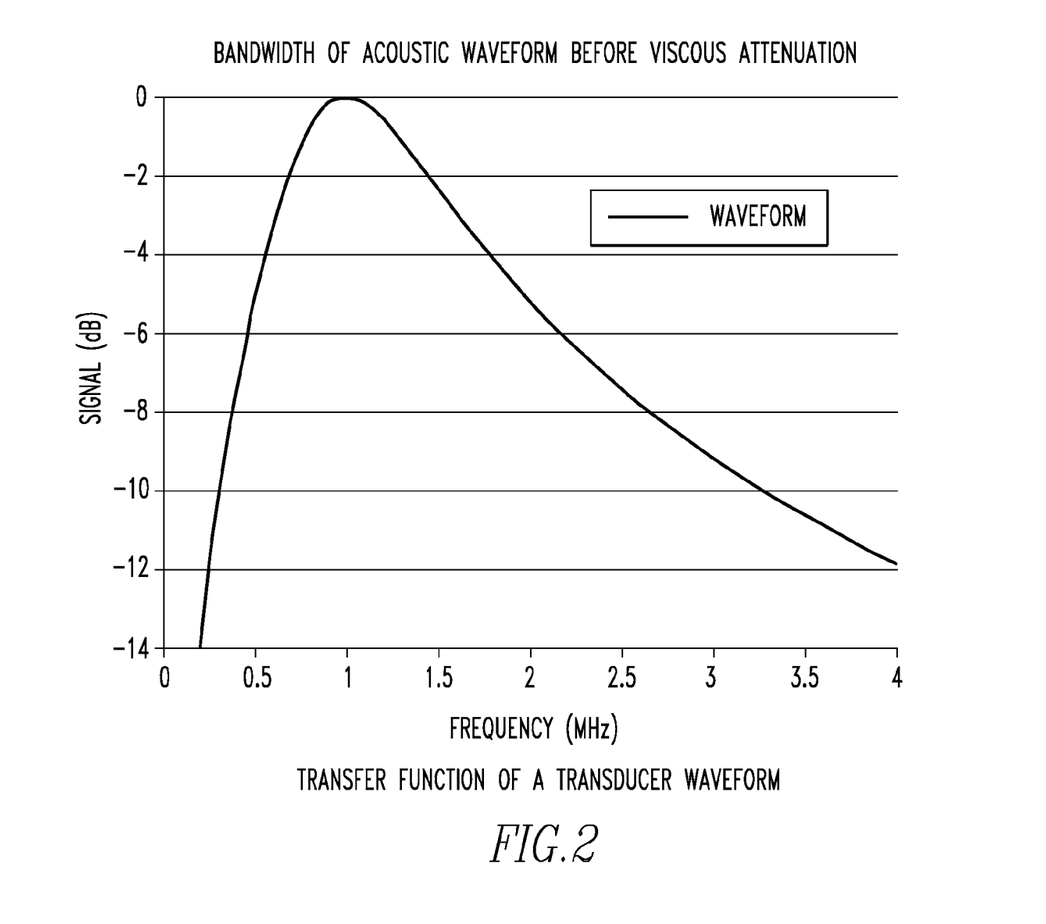
FIG. 2 shows a transfer function of a transducer waveform.

Examples of the attenuation versus frequency expected due to viscous losses is shown for a 12 inch path length in FIG. 1.

Excitation/Transmission

The excitation of the transmitting transducer 2 is provided by an impulse signal with broad spectrum bandwidth. The use of an impulse is not a requirement, in fact, using a rectangular pulse is typical, but for the sake of simplifying the math here, an impulse is used (e.g., frequency response is 1 for all frequencies).

Transmitting and Receiving Transducers

The transmitting and receiving transducers 2, 4 are nominally identical and therefore reciprocal. The transfer function of the transducer proper is characterized as the current response to a voltage impulse input to an R, L, C circuit where the R describes the energy transduced and transmitted to the adjacent medium, L, the inertial mass of the transducer material and C its stiffness; see Kinsler and Frey, previously cited. The use of reciprocal transducers is not a requirement but is shown to simplify the analysis.

This simplified model leads to the transfer function of a classic underdamped second order system, expressed as a function of the angular frequency $\omega$ normalized to the transducer resonant frequency, $\omega_0$ $$G(jw) = \frac{j2\zeta\omega\omega_0}{-\omega^2 + \omega_0^2 + j2\zeta\omega\omega_0} \quad 4)$$

Here
G(jw)=transducer's transfer function
$\omega$=natural frequency of the transducer
$\zeta$=damping coefficient for the transducers
j=square root of $-1$ The transfer function for the combination of the transmitting transducer 2 and the receiving transducer 4 is the square of the transfer function of equation 4:

$$G(jw)^2 = \frac{-(2\zeta\omega\omega_0)^2}{(-\omega^2 + \omega_0^2)^2 - (2\zeta\omega\omega_0)^2} \quad 5)$$

An example of such a transfer function is shown in FIG. 1. For this figure, the damping coefficient was taken as 0.5 and the center frequency is taken as 1 MHz.

The Receiver Input Circuit

The shape of the received signal is also affected by a series capacitance—resistance circuit at the receiver 4 input, which couples alternating electrical current from the receiving transducer 4 to the first stage of the receiver 4. For simplification, the receiver 4 is also assumed to have a flat passband (e.g., frequency response is 1 for all frequencies).

Analytical Results—Frequency Shift as Function of Viscosity

The transfer function of the transmitter-transducer-attenuating fluid-transducer-receiver input circuit is the product of the transfer functions of the individual elements:

$$H(w) = \frac{-(2\zeta\omega\omega_0)^2}{(-\omega^2 + \omega_0^2)^2 - (2\zeta\omega\omega_0)^2} Av(\omega) \quad 6)$$

Figure 3:
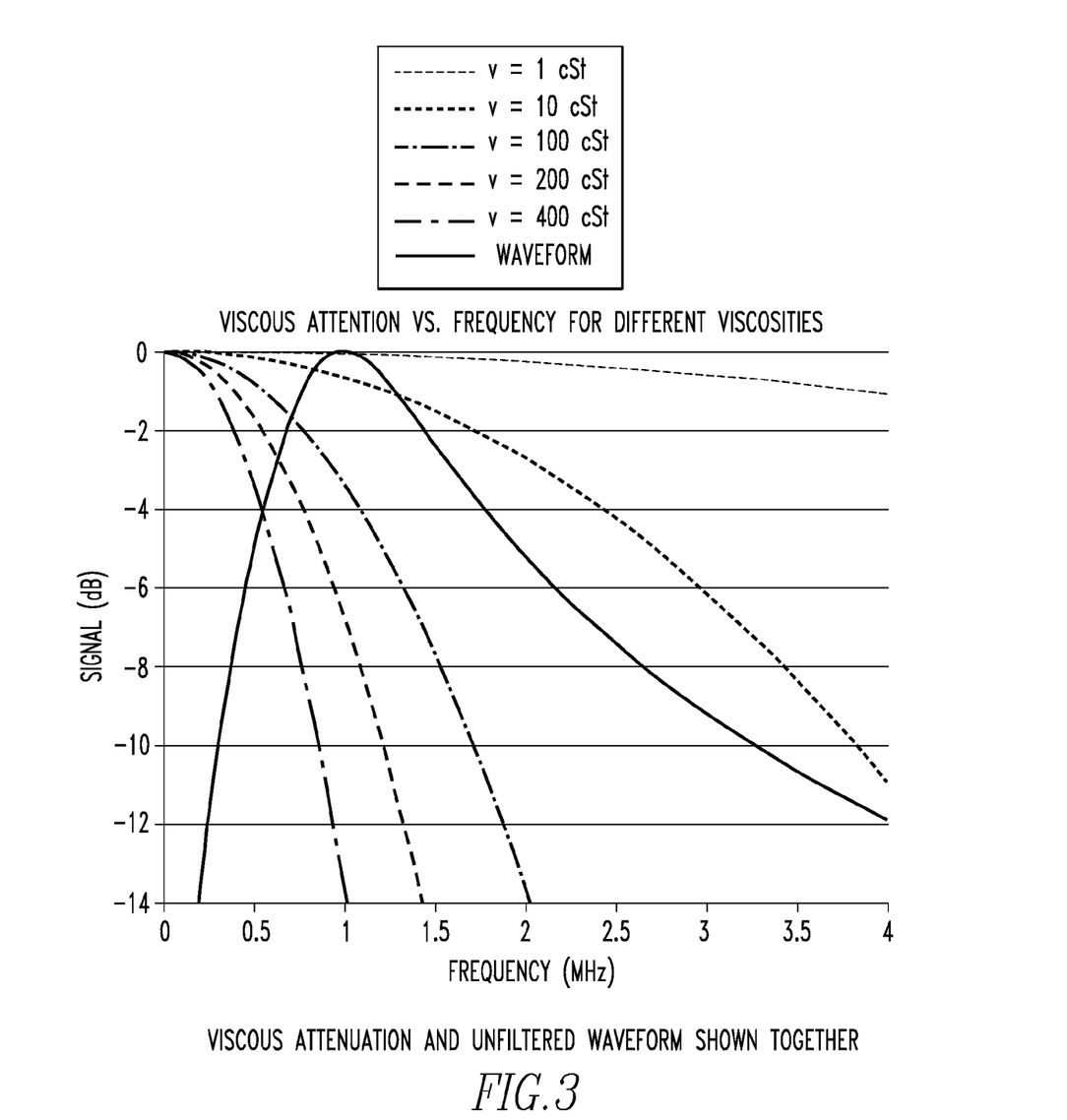
FIG. 3 shows viscous attenuation and unfiltered waveform together.

FIG. 3 shows the calculated transfer function of the acoustic waveform without viscous attenuation and the attenuation produced by a range of viscosity-path length conditions (The viscosity path length product is used because the attenuation of the energy is a function of the product of the attenuation factor (which in turn contains sound velocity, frequency and viscosity) and the path length. For the graph, the path length is 12 inches and the sound velocity is 50,000 in/s.)

Figure 4:
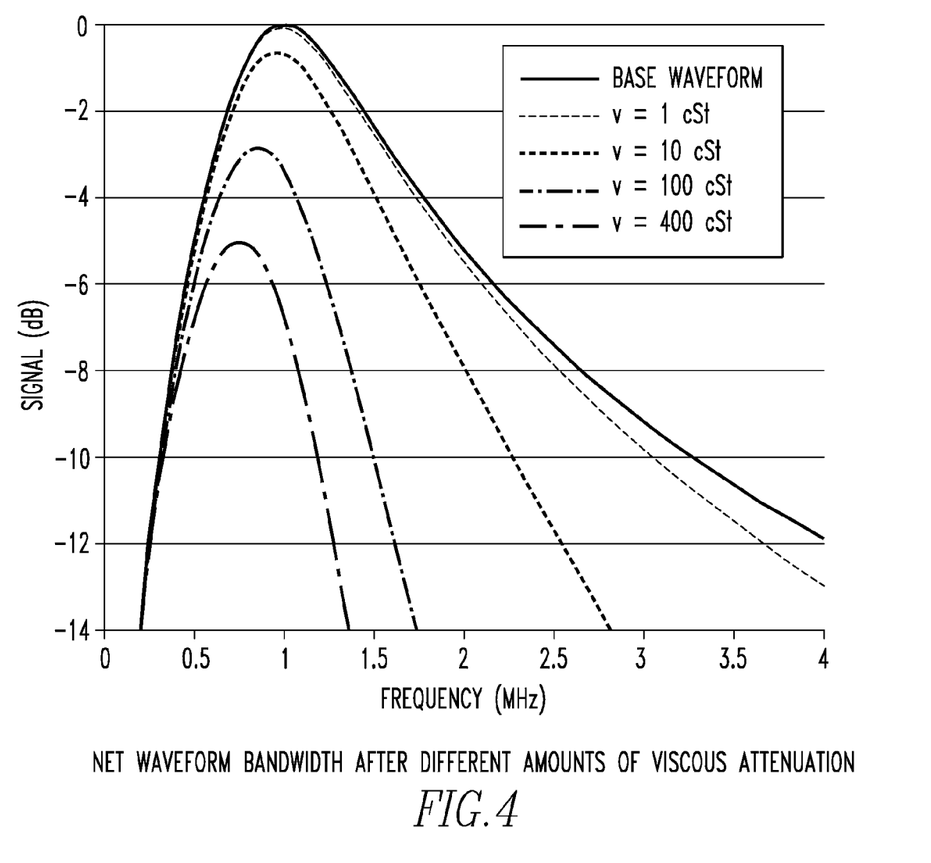
FIG. 4 shows net waveform bandwidth after different amounts of viscous attenuation.

The net waveform response including attenuation is the product of the waveform's transfer function without viscous attenuation and the transfer function characterizing the viscous attenuation for the specific conditions under investigation. FIG. 4 provides examples of the net bandwidth.

Figure 5:
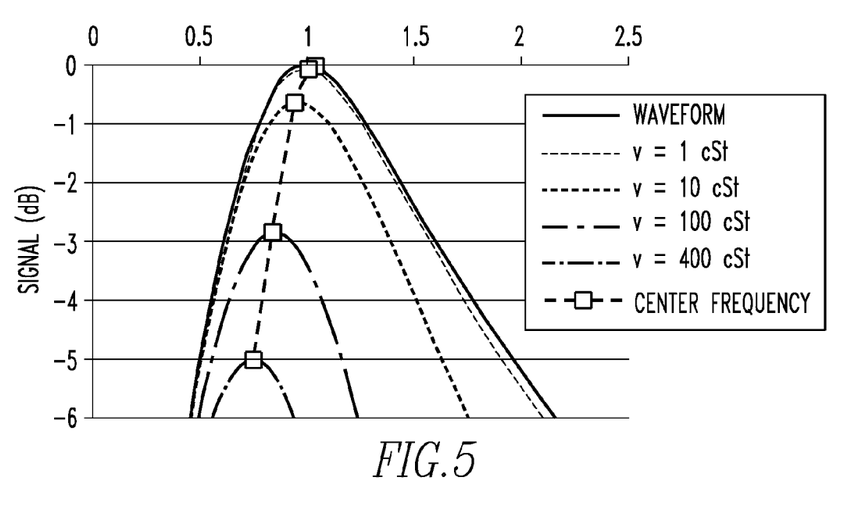
FIG. 5 is a graph of the net waveform's center frequency calculated from the median frequency for each of the responses of FIG. 4.

The net waveform's center frequency has been calculated from the median frequency for each of the responses of FIG. 4 is graphed in FIG. 5. Another method would be to take the inverse transforms of the transfer functions of FIG. 4. For the cases where viscous attenuation is significant, the procedure is reasonably accurate, since the composite transfer functions are approximately symmetrical about the peak.

Experimental Results

Data for both low and high viscosity oils have been analyzed to confirm that the means disclosed herein can accommodate a wide range of viscosities.

Data were drawn from two sources:

(a) Data set 1: Measurements in the calibration lab of frequency shifts on an 8 inch ultrasonic meter having 1.6 MHz transducers, a 20 inch ultrasonic meter having 1.0 MHz transducers, and a 24 inch ultrasonic meter having 1.0 MHz transducers. 16 separate measurements of frequency shift were made for viscosities ranging from 1 cSt (water) to about 86 cSt.

(b) Data Set 2: Measurements made in a special test rig which allowed the distance between transmitting and receiving transducers 2, 4 to be varied. The rig was filled with liquid water (for reference) and with oils having viscosities of 300, 1120 and 4000 cS. Distances were varied from 4 inches to 45 inches except for the heaviest oils, where a weak received signal limited the maximum distance to 25 inches.

The technique described here defines a Frequency Parameter FP that is based on the analysis of the previous section and is closely correlated with the fluid viscosity. The form and preliminary values of the constants of the correlation between the frequency parameter and the viscosity are given herein. The values of the constants of the correlation can be enhanced during the factory acceptance tests and calibrations.

To enhance the accuracy of the viscosity determination, the Frequency Parameter—the independent variable of that determination—should incorporate those variables that an ultrasonic flowmeter can measure in real time in the field and that can affect viscous attenuation, as well as those variables that can be measured in factory acceptance tests (e.g. received signal frequency without significant viscous attenuation).

Equation (6) determines the frequency change brought about by the attenuation of transmitted ultrasound in a viscous medium, as against the attenuation in a medium of low viscosity. The equations lead to the following definition for the frequency parameter FP:

$$FP = (1/v_0)(C_0/C)^3 (f/f_0)^2 \quad \text{Equation (4)}$$

The zero subscripted variables in the Frequency Parameter are those measured with water (reference fluid); the variables without subscripts are measured in real time. If the viscosity is measured as an adjunct of a flow measurement these variables are measured concurrent with the volumetric flow measurement of the medium having unknown viscosity.

The Frequency Parameter has been calculated for the data sets referenced above, a total of 41 data points. The logarithms, to the base 10, of the viscosity—path length products (Again, the frequency parameter is correlated with the product because the attenuation of the energy is a function of the product of the attenuation factor (which in turn contains sound velocity, frequency and viscosity) and the path length) measured for those data sets are plotted against the Frequency Parameters for the data in FIG. 6. A logarithm is selected for the ordinate because of the form of Equation (1), which shows the viscous attenuation to be an exponential function of the viscosity—path length product. The fit of these data can be used to determine an unknown product viscosity. The Frequency Parameter, whose inputs are measured concurrently with the measurement of the flow of a fluid having an unknown viscosity and, for the 0 subscripted variables, in FAT tests, would be entered into the data fit algorithm to determine the log to the base 10 of the viscosity path length product. The base of the logarithms (10) would be raised to the numerical value of the log (i.e. the power) found using the fit, and that result divided by the (known) path length to determine the viscosity.

Figure 6:
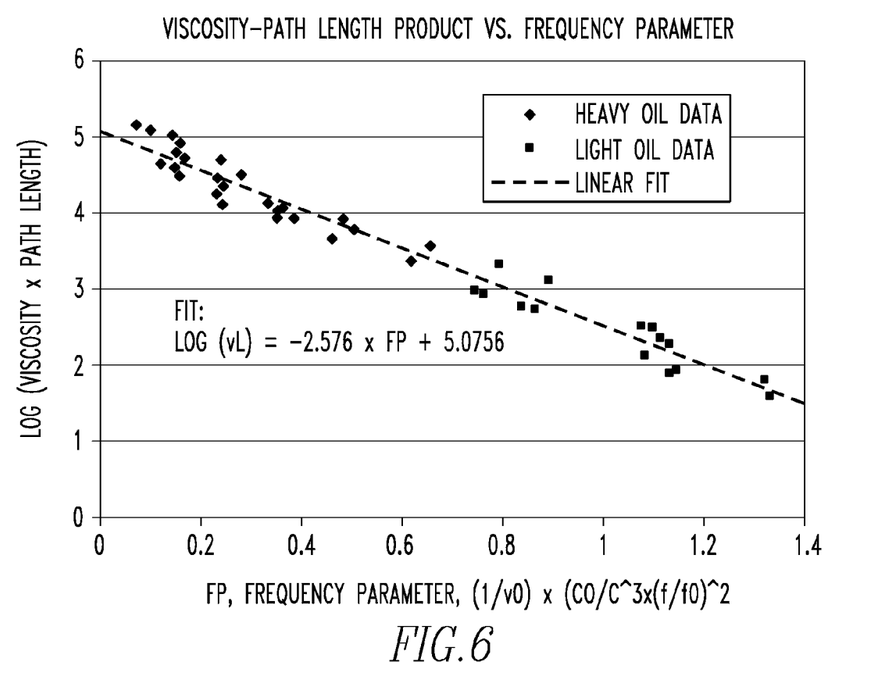
FIG. 6 is a graph of log (viscosity×path length) USFP.

From the data of FIG. 6 the following conclusions are drawn:

1. The linear fit of the two variables shown in the figure correlates the data well. The extent of the fit is excellent—kinematic viscosities range from 2.5 to 4000 cSt, and comprise 6 different oils.

2. The fit is expressed as follows:

$$\text{Log}_{10}(vL_{path}) = m \times (FP) + b.$$

Where m=−2.576
b=5.0756

3. One standard deviation of the data about the linear logarithm fit of FIG. 6 is about ±0.18 (units are Log to the base 10 of the viscosity-path length product).

4. The departures of the individual data sets from the fit are tabulated below:

| Nominal viscosity of test oil cS | Number of data points | Average deviation from fit of all data points, Log (v L) |
|---|---|---|
| 2.5 | 2 | +0.05 |
| 12 | 8 | +0.001 |
| 80 | 6 | +0.009 |
| 300 | 9 | −0.095 |
| 1120 | 9 | −0.096 |
| 4000 | 7 | +0.22 |

The large deviation of the 4000 cS data set may be due to the weakness of the received signal with this oil. The weak signal, in combination with coherent noise, will produce distortion, which can introduce biases in the measurement of the received signal frequency and therefore in the Frequency Parameter. If the 4000 cS data are excluded the standard deviation of the fit is reduced to ±0.15 (log to the base 10 units).

Description of the Apparatus

FIG. 7 shows an example of the apparatus 100 for carrying out the viscosity measurement as described herein. The figure shows the most rudimentary embodiment; more sophisticated embodiments will also be described.

The measurement is initiated by triggering a transmitter 1) which generates an electrical pulse. Simultaneous with the transmission of the pulse, counting of timing pulses from a digital clock 30 will commence. The timing pulse count will stop at later times in the process as will be described below.

The transmitter pulse will be connected via electrical cables to an ultrasonic transducer 2. Electrical connections are shown as solid lines in FIG. 7. Dashed lines indicate mechanical connections. Hatched lines indicate related digital computations. The application of the pulse to the transmitting transducer 2 causes that device to produce an ultrasonic pressure pulse having a limited number of sinusoidal cycles (3 to 5). The period of the sinusoid is set by the interaction of the broad spectrum of the pulse and the "natural period" of the transmitting transducer 2. The natural period of the transmitting transducer 2 is set by its dimensions and the speed of sound in the transducer material.

The ultrasonic transmitting transducer 2 is mounted such that the ultrasonic energy it produces is transferred to the fluid whose viscosity is to be measured. The ultrasonic energy travels through the fluid along a path 3 of known length, L.

At the end of the path 3, some of this energy is transferred to a receiving transducer 4, having characteristics similar to the transmitting transducer 2. The receiving transducer 4 converts some of the ultrasonic energy into an electrical pulse.

The path 3 through the viscous fluid and each interface in the acoustic path 3 diminishes the electrical energy of the received ultrasonic pulse. Accordingly the received signal is amplified by a receiver 5, whose frequency response is such that the energy content of all frequencies that are present in the received signal is preserved. Because of this characteristic the receiver 5 is said to be "broad band".

The received signal is digitized in a digitizer 6, an analog to digital converter employing a sample frequency higher, by order of magnitude or more, than the natural frequency of the transducers.

The signal is then reconstructed in digital format by a computer 20 and the time of its arrival is detected by signal detection logic 7 of the computer 20. Details of the detection logic itself are not shown and are not unique to this invention and are well known. In summary, the $1^{st}$ large half cycle of the received signal is detected when a signal of magnitude greater than an enabling threshold is received. The time at which the next zero crossing of the received signal occurs, $t_1$ is measured using the count of timing pulses that was initiated when the transmitter 1 applied the pulse to the transmitting transducer 2. Also measured is $t_2$, the time of the zero crossing following $t_1$. The $t_2$ measurement also uses the count of timing pulses occurring between transmission and this zero crossing.

The times measured include not only the transit time through the viscous fluid but also the transit times through the non-fluid media of the energy transmission path 3, such as the electrical delay of the cable between the transmitter 1 and the transmitting transducer 2, the mechanical delay associated with the interface between the transmitting transducer 2 and the viscous fluid, the mechanical and cable delays associated with the receiving transducer 4 and the electronic delays of the receiver 5. These last include the delay between the leading edge of the received signal and the zero crossing at which $t_1$ is measured. The delays in the non-fluid media must be accounted in the signal processing described below. The delays can be calculated or measured as part of the calibration process by means that are not unique to this invention.

The digital signal processing 8 calculates the sound velocity of the fluid having unknown viscosity as the quotient of the path 3 length L through which the ultrasound has traveled and the transit time of the ultrasound in the fluid. The transit time of the ultrasound in the fluid is given by the difference between the measured time $t_1$ and sum of the delays in non-fluid media, $\tau$. The signal processing 8 also calculates the dominant frequency of the received signal as the reciprocal of period of that signal. The period of the received signal is taken as twice the difference between the time of the zero crossing of the half cycle following signal detection, $t_2$ and the time of the zero crossing of the trailing edge of the detection half cycle $t_1$. There is no need to subtract non fluid delays from the time measurements used to determine period because the same delays are present in both measurements.

In many applications the fluid for which the viscosity to be measured will be flowing. As a consequence some component of fluid velocity will project onto the acoustic path 3. In such cases counterpropagation of acoustic pulses through the fluid will be employed. Counterpropagation employs a multiplexer to initiate acoustic pulse propagation first in one direction (such as that shown in FIG. 7) then in the other, using what was previously the receiving transducer 4 as the transmitting transducer 2 and processing the signal received on what was previously the transmitting transducer 2. Counterpropagation makes use of the reciprocal nature of the acoustic path 3 and the similar characteristics of the transmitting and receiving transducers 2 and 4. It is often employed in transit time ultrasonic flowmeters, because the difference in transit times in the upstream and downstream directions along an acoustic path 3 provides a measure for the fluid velocity projected onto that path 3. In the case of this invention, using the average of transit times $t_{1up}$ and $t_{1down}$ of counterpropagated pulses eliminates any error in sound velocity due to the presence of a non-zero fluid velocity.

The results of the sound velocity and received frequency measurements are used to calculate a frequency parameter FP by the FP calculation module 9. For this computation, many samples of the measured sound velocity and received signal frequency may be employed to reduce errors due to the width of the clock 30 pulses, turbulence and random electrical noise that may be present in a single sample. Baseline data taken during acceptance testing and calibration of the apparatus 100 (which is also considered an ultrasonic flow meter) are also employed in the calculation of the frequency parameter. These data include a viscosity $v_0$ for a low viscosity fluid for which the frequency $f_0$ and sound velocity $C_0$ are also measured.

The Frequency Parameter used with a log linear characteristic to determine the Logarithm of the viscosity path length product Log (vL) by the log (VL) calculation module 10. The constants of the Log linear characteristic—the slope m and the offset b—are established during the process of calibrating the system in the laboratory, by measuring the half period of the received signal and the sound velocity for fluids of known viscosity.

The viscosity v is then calculated by subtracting the logarithm of the path length from the Log (vL), then taking the antilog by the viscosity calculation module 11.

FIG. 8 is a flow chart of the implementation of the technique disclosed herein as applied to the determination of Reynolds Number.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

The invention claimed is:

1. An apparatus for determining a fluid's kinematic viscosity comprising:
   a transmitter and a transmitting transducer capable of converting a single pulse from the transmitter into ultrasonic energy;
   a receiving transducer and an electronic amplifier which converts some of the ultrasonic energy that has passed through a fluid of unknown viscosity into an electrical signal, the ultrasonic energy created by the transmitting transducer follows an acoustic path which is made to pass through the fluid of unknown viscosity along a path of known length; and
   a computer which determines a characteristic frequency of a received electrical signal and measures a fluid's velocity of sound and which determines kinematic viscosity of the fluid on a continuous basis based on the characteristic frequency and the sound velocity, where the kinematic viscosity is formed from a fluid's bulk viscosity and shear viscosity.

2. The apparatus of claim 1 wherein the fluid's bulk viscosity has a fixed relationship with the fluid's shear viscosity.

3. The apparatus of claim 2 wherein the computer combines the characteristic frequency and sound velocity with similar data measured for a fluid of different viscosity and sound velocity to form a frequency parameter, the data having been measured as part of a calibration process of the apparatus.

4. The apparatus of claim 3 wherein the computer determines a Logarithm to an arbitrary base of a viscosity-path length product for the fluid of unknown viscosity from the frequency parameter and from the data taken during calibration of the apparatus, the frequency parameter and the data used by the computer to establish a slope and offset of the Logarithm to the arbitrary base of a viscosity-path length product versus frequency parameter relationship.

5. The apparatus of claim 4 wherein the computer subtracts a logarithm of the path length from a logarithm of the viscosity path length product to yield a result, and the computer takes an antilog of the result, thereby determining the kinetic viscosity of the fluid.

6. A method for determining a fluid's kinematic viscosity comprising the steps of:
- triggering a transmitter which generates an electrical transmit pulse;
- commencing counting of timing pulses from a digital clock simultaneous with a transmit pulse transmission;
- applying the transmit pulse via electrical cables to an ultrasonic transmitting transducer;
- causing the transmitting transducer with the transmit pulse to produce an ultrasonic pressure pulse having a limited number of sinusoidal cycles, the ultrasonic transmitting transducer is mounted such that ultrasonic energy the transmitting transducer produces travels through a fluid whose viscosity is to be measured along a path of known length;
- transferring at an end of the path some of this energy to a receiving transducer;
- converting with the receiving transducer some of the ultrasonic energy into an electrical receive pulse;
- amplifying by a receiver the receive pulse whose frequency response is such that the energy content of all frequencies that are present in the receive pulse is preserved;
- digitizing in a digitizer the receive pulse, an analog to digital converter employing a sample frequency higher, by order of magnitude or more, than the natural frequency of the transmitting transducer and the receiving transducer;
- reconstructing the receive pulse in digital format;
- detecting a time of the receive pulse's arrival by signal detection logic;
- measuring with a computer a transit time through the viscous fluid of a pressure pulse and a transit time through non fluid media of an energy transmission path, including electrical delay of the cable between the transmitter and the transmitting transducer, mechanical delay associated with an interface between the transmitting transducer and the fluid, mechanical and cable delays associated with the receiving transducer and electronic delays of the receiver;
- calculating a fluid's sound velocity as a quotient of the path length L through which the ultrasonic energy has traveled and the transit time of the ultrasonic energy in the fluid;
- calculating a frequency parameter FP from the sound velocity and frequency measurements of a received ultrasonic energy pulse;
- determining a Logarithm of a viscosity path length product Log (v L) with the computer from the Frequency Parameter with a log linear characteristic; and
- calculating with the computer a kinematic viscosity v by subtracting the logarithm of the path length from the Log (v L) to obtain a reminder, then taking an antilog of the reminder.

7. The method of claim 6 wherein the fluid is flowing.

8. The method of claim 7 wherein the fluid's bulk viscosity has a fixed relationship with the fluid's shear viscosity.

9. The apparatus of claim 1 wherein the fluid is flowing.

10. An apparatus for determining a fluid's kinematic viscosity comprising:
- a transmitter and a transmitting transducer capable of converting a single pulse from the transmitter into ultrasonic energy;
- a receiving transducer and an electronic amplifier which converts some of the ultrasonic energy that has passed through a fluid of unknown viscosity into an electrical signal, the ultrasonic energy created by the transmitting transducer follows an acoustic path which is made to pass through the fluid of unknown viscosity along a path of known length;
- a computer which determines a characteristic frequency of a received electrical signal and measures a fluid's velocity of sound and which determines kinematic viscosity of the fluid on a continuous basis based on the characteristic frequency and the sound velocity, where the kinematic viscosity is formed from a fluid's bulk viscosity and shear viscosity, the bulk viscosity has a fixed relationship with the shear viscosity, the computer combines the characteristic frequency and the sound velocity with similar data measured for a fluid of different viscosity and sound velocity to form a frequency parameter, the data having been measured as part of a calibration process of the apparatus, the computer determines a Logarithm to an arbitrary base of a viscosity-path length product for the fluid of unknown viscosity from the frequency parameter and from the data taken during the calibration of the apparatus, the frequency parameter and the data used by the computer to establish a slope and offset of the Logarithm to the arbitrary base of a viscosity-path length product versus frequency parameter relationship.

* * * * *